(12) United States Patent
Jain

(10) Patent No.: US 6,470,305 B1
(45) Date of Patent: Oct. 22, 2002

(54) CHEMICAL ANALYSIS BY MORPHOLOGICAL SIMILARITY

(76) Inventor: Ajay N. Jain, c/o Iconix Pharmaceuticals Inc., 850 Maude Ave., Mountain View, CA (US) 94043

( * ) Notice: Subject to any disclaimer, the term of this patent is extended or adjusted under 35 U.S.C. 154(b) by 0 days.

(21) Appl. No.: 09/475,413

(22) Filed: Dec. 30, 1999

Related U.S. Application Data

(60) Provisional application No. 60/114,403, filed on Dec. 31, 1998.

(51) Int. Cl.[7] .............................................. G01N 33/00
(52) U.S. Cl. ...................................................... 703/22
(58) Field of Search ............................................ 702/22

(56) References Cited

PUBLICATIONS

Jain, A.N., "Scoring Noncovalent Protein–Ligand Interactions: A Continuous Differentiable Function Tuned to Compute Binding Affinities," *J. Comp–Aided Mol. Des.* 10:427–440 (1996).

Jain et al., "Quantitative Binding Site Model Generation: Compass Applied to Multiple Chemotypes Targeting the 5–HT$_{1A}$ Receptor," *J. Med. Chem.* 38:1295–1307 (1995).

Jones et al., "Development and Validation of a Genetic Algorithm for Flexible Docking," *J. Mol. Biol.* 267:727–748 (1997).

Welch et al., "Hammerhead: Fast, Fully Automated Docking of Flexible Ligands to Protein Binding Sites," *Chem. And Biol.* 3:499–462 (1996).

Willett et al., "Implementation of Nonhierarchic Cluster Analysis Methods in Chemical Information Systems: Selection of Compounds for Biological Testing and Clustering of Substructure Search Output," *J. Chem Inormation and Computer Sci* 26:109–118 (1986).

*Primary Examiner*—Michael Borin
(74) *Attorney, Agent, or Firm*—Robins & Pasternak LLP

(57) ABSTRACT

The similarity between two molecules is computed by providing a set of points around each molecule equidistant from the surface, calculating the distance from each point to the molecular surface, and to the nearest hydrogen bond acceptor and donor, identifying triplets (triangles) of points around each molecule that have identical weightings, and superimposing identical triangles.

4 Claims, 9 Drawing Sheets

US 6,470,305 B1

CHEMICAL ANALYSIS BY MORPHOLOGICAL SIMILARITY

RELATED APPLICATIONS

This application is based on U.S. Ser. No. 60/114,403, filed Dec. 31, 1998, incorporated herein by reference in full.

FIELD OF THE INVENTION

This invention is related to the fields of drug design and computational chemistry. More particularly, the invention relates to methods and devices for calculating and predicting the functional behavior of different molecules based on molecular similarity.

BACKGROUND OF THE INVENTION

Structure-based drug design has produced some success stories in the area of prospective rational design of high-affinity ligands, particularly in the case where an X-ray structure of the biological target protein has been available and docking approaches such as Hammerhead and DOCK are applicable. More often, however, a high-resolution structure of an interesting target protein is not available. In these cases, computational techniques for molecular diversity optimization of screening libraries as well as techniques for three-dimensional quantitative structure-activity (3D QSAR) modeling become important. These techniques require methods of quantitative and/or geometric comparison between pairs of molecules.

Molecular diversity optimization requires a metric for estimating the relative redundancy of one molecule compared to another. For the problem of designing a library of molecules to screen against a variety of biological targets, the relevant notion of redundancy is the degree to which one molecule is likely to bind the same sites as another. Several popular methods for molecular diversity optimization rely on topological diversity in the space of two-dimensional molecular representations and are based on the work of Willett et al., *J. Chem Information and Computer Sci* (1986) 26:109-18.

FIG. 1 illustrates the problem with an example reported by Y. Martin et al., "Experience with the Application of Computers to Library Design", *Cambridge Heath-tech Institute's Second Annual Conference on Chemoinformatics* (1998). Nicotine and several analogs are shown along with a known oxazole-containing nicotinic agonist and acetylcholine, the natural ligand. The molecules are listed in order of decreasing similarity, according to the Tanimoto coefficient of their 2D fingerprints, as implemented in the Daylight software package (referred to herein as the "topological method"). Note that the simple nicotine analogs show high computed similarity to nicotine. However, a known, potent, competitive ligand with obvious structural similarity has low computed similarity, and the natural ligand is judged to be unrelated using this metric.

While there have been some attempts at three-dimensional approaches to the diversity optimization problem, none have successfully addressed the fundamental issue, that of the pairwise distance measure and its relationship to the biological functional relatedness of molecules. To the extent that a method can predict likely geometric relationships of molecules in the context of binding to protein active sites, it may also have applicability to the 3D QSAR problem.

SUMMARY OF THE INVENTION

A new method for rapidly comparing two molecules and determining a measure of similarity having biological relevance has now been invented.

One aspect of the invention is a method for comparing two molecules to predict if they will exhibit similar biological activities, by providing a set of reference points having reference coordinates, computing a molecular surface for a first molecule, determining the distance from each reference point to the molecular surface to provide a first set of distances, computing a molecular surface for a second molecule, determining the distance from each reference point to the second molecular surface to provide a second set of distances, and calculating the difference between the first set and second set of distances to determine the difference between the first molecular surface and the second molecular surface.

Another aspect of the invention is a system for comparing two molecules to predict if they will exhibit similar biological activities, comprising an input means for providing a set of reference points having reference coordinates; computation means for computing a molecular surface for a first molecule and determining the distance from each reference point to the molecular surface to provide a first set of distances, computing a molecular surface for a second molecule, determining the distance from each reference point to the second molecular surface to provide a second set of distances, and calculating the difference between the first set and second set of distances to determine the difference between the first molecular surface and the second molecular surface; storage means for storing intermediate and final results; and output means for displaying the results.

Another aspect of the invention is a machine-readable medium having stored a set of instructions capable of causing an appropriate machine to accept a set of reference points having reference coordinates, compute a molecular surface for a first molecule, determine the distance from each reference point to the molecular surface to provide a first set of distances, compute a molecular surface for a second molecule, determine the distance from each reference point to the second molecular surface to provide a second set of distances, and calculate the difference between the first set and second set of distances to determine the difference between the first molecular surface and the second molecular surface, thereby determining the morphological similarity between two molecules.

DETAILED DESCRIPTION

General Method

Figure 1:
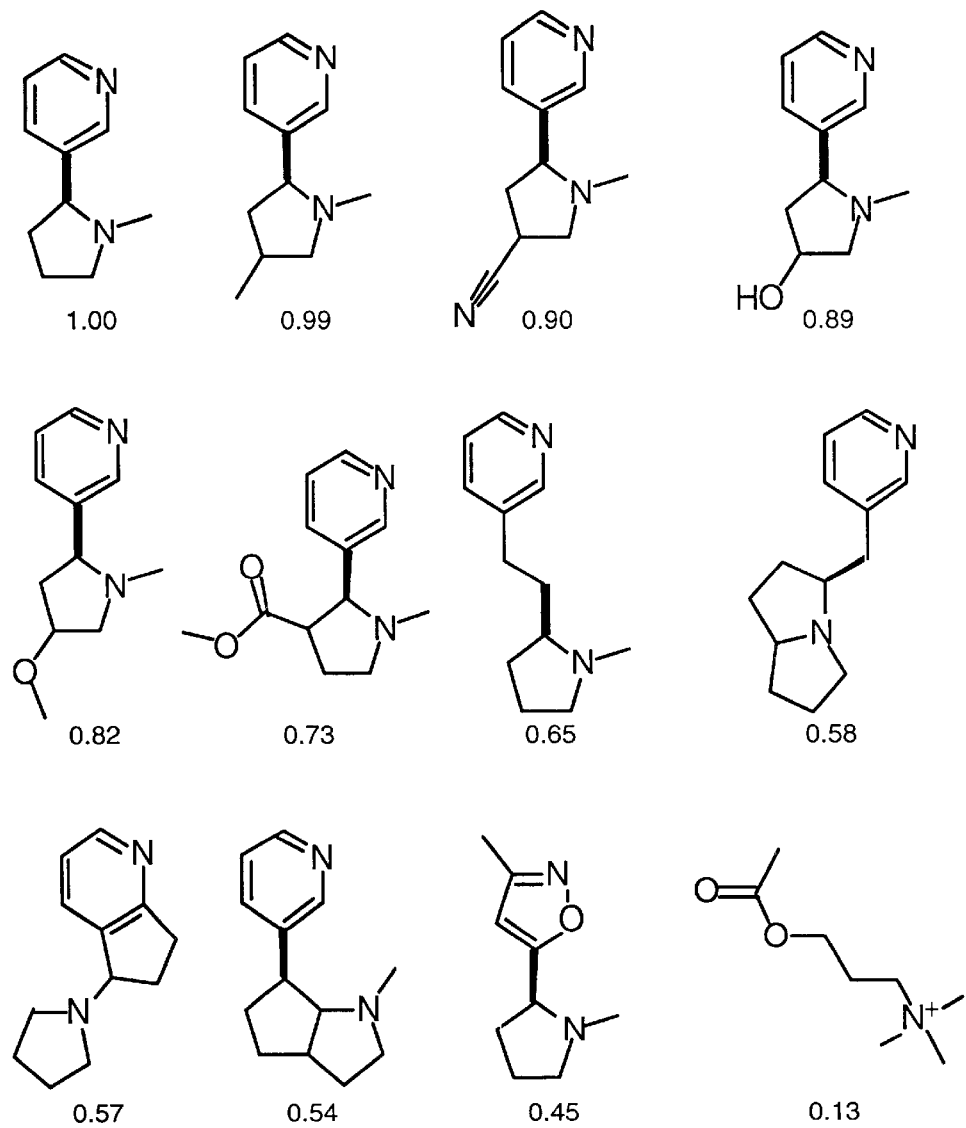
FIG. 1 shows the structural formulae for the compounds examined by Y. Martin et al., along with their similarity rankings according to the Tanimoto coefficient of their 2D fingerprints.
Figure 2:
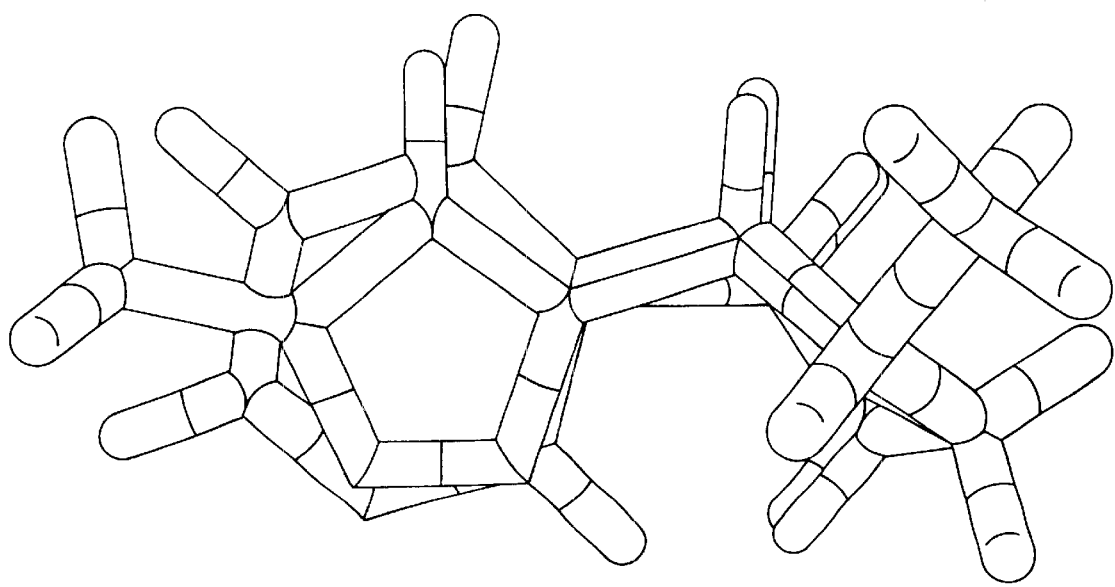
FIG. 2 shows nicotine and an oxazole derivative superimposed by morphological similarity.

The instant method is based on the principle that most biological molecular interactions depend on the surface morphology and charge distribution of two or more interacting surfaces. Although hydrogen-bonds and salt bridges are known and modeled relatively easily, hydrophobic interactions often account for the affinity of a specific interaction. Prior art methods for estimating the similarity of two molecules generally focus on the backbone and the functional groups present on each molecule, more or less ignoring the three-dimensional shape of the molecules. In contrast, the method of the invention compares the 3D shape of the molecules, regardless of the "internal structure" of the molecules. The result is that the method of the invention provides a much more useful measure of similarity, a measure that correlates with biological activity to a high degree. FIG. 2 shows nicotine and the oxazole derivative from FIG. 1 superimposed. The conformation and alignment shown maximizes the morphological similarity function. Note that the protonated amines are coincident, and that the pyridine nitrogen and oxazole nitrogen are capable of accepting a hydrogen-bond from the same part of space. The critical observation in defining the similarity function and its optimization method is that the molecules shown in FIG. 2 look roughly the same from the same observation points in space, at least with respect to their surface shapes and disposition of charge.

Figure 3:
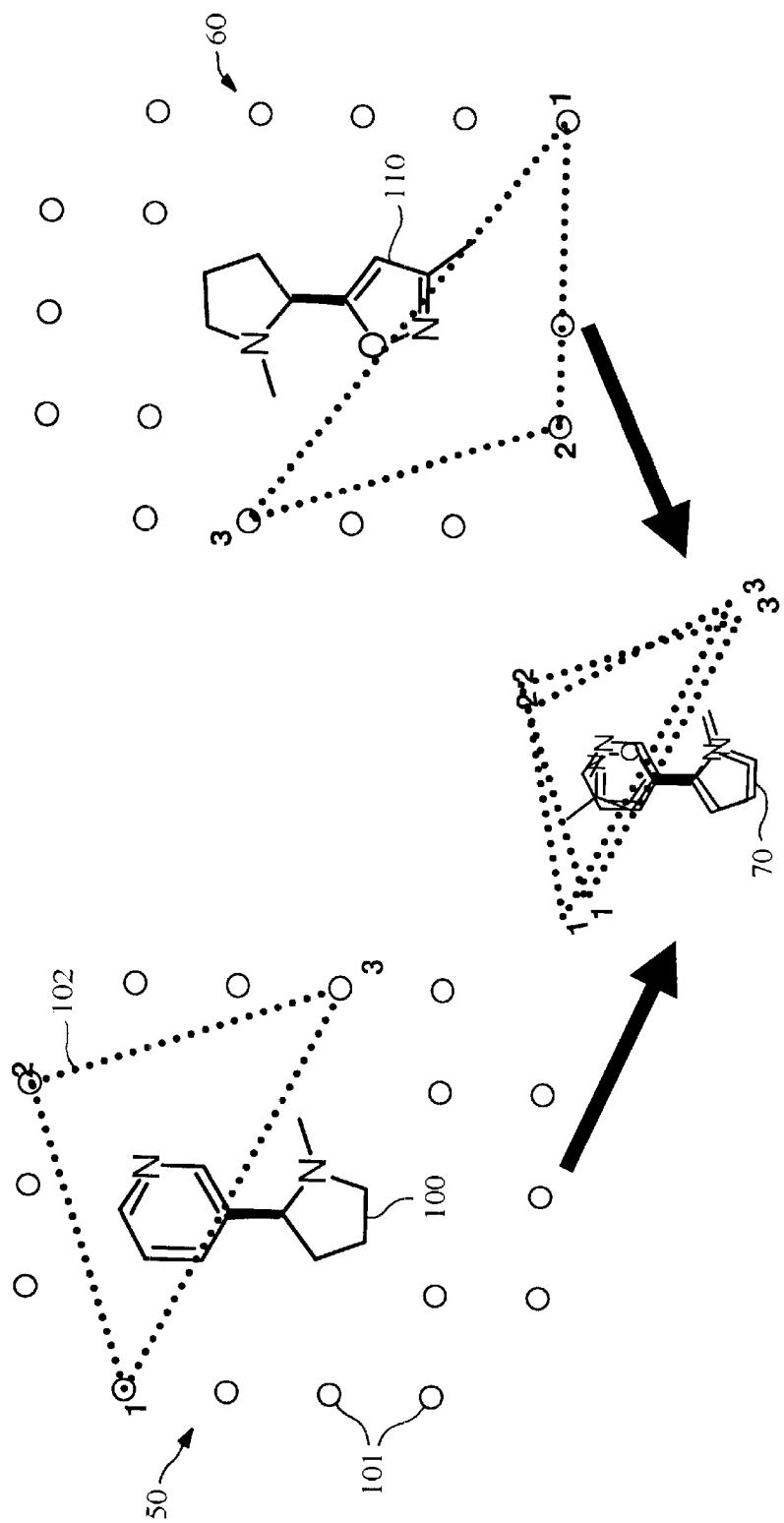
FIG. 3 depicts two molecules surrounded by observation points, and their alignment using similar triangles.

Morphological similarity is defined as a Gaussian function of the differences in molecular surface distances of two molecules at weighted observation points on a uniform grid. A variety of methods can be employed to produce or calculate a number of different forms of molecular surface, for example Van der Waals radii, Connolly surfaces, electron density isosurfaces, and the like. Importantly, the observations made are not dependent on the absolute coordinate frame. So, two unaligned molecules that have some degree of similarity will have some corresponding set of observers that are "seeing" the same things. Optimization of the similarity of two unaligned molecules is performed by finding sets of observers of each molecule that form triangles of the same size, where each pair of corresponding points in the triangles are observing similar features. The transformation that yields a superposition of the triangles will tend to yield high-scoring superpositions of the molecules. FIG. 3 illustrates two molecules 100, 110, surrounded by observation points 101, three of which form corresponding triangles 102 that are superimposed to provide an optimal alignment 70.

In general, a molecule of interest is first modeled computationally using standard methods, for example using force field calculations. Any generally suitable model may be employed, as long as it provides a reasonably accurate or predictive a low-energy conformation of the molecule. The examples herein employ a calculated Van der Waals ("VdW") surface. If the molecule is complex (for example, if it contains more than a few rotatable bonds), it may be fragmented, and each fragment computed separately (and reassembled later).

The molecular representation is then embedded in a set of reference points, which can comprise any suitably dense array of points, such as a regular three-dimensional array, an array of randomly spaced points, and the like. The reference points are spaced apart at a distance that provides sufficient resolution for examination of the subject molecule, but not so close as to unduly increase computation time. Reference point spacings of about 0.5 Å to about 5.0 Å are preferred for comparison of small or medium sized molecules, particularly spacings of about 2.0 Å. Larger molecules, such as proteins, catalytic surfaces, and the like, may be examined using a grid with a larger spacing (and lower resolution) in order to reduce the required computation time, if desired. The reference points around the molecule are then weighted or selected according to a distribution function such as a Gaussian function, to provide a set of points forming a shell approximately equidistant from the surface of the molecule. The thickness of the shell will depend on the breadth of the distribution function selected. In general, the shell should be at least about 0.1 Å from the molecular surface, more preferably at least about is 1.0 Å, and preferably no further than about 1,000 Å, more preferably less than about 100 Å, most preferably about 4 Å. Increasing the thickness of the shell, and/or the size of the shell, increases the number of calculations to compute. At each point, the minimum distance to the VdW surface is computed. The minimum distance to a hydrogen-bond acceptor (or negatively charged atom) and the minimum distance to a hydrogen-bond donor (or positively charged atom) is also preferably calculated. Where distances to hydrogen-bond acceptors and/or donors are calculated, it is also advantageous to calculate the directionality of the hydrogen bond. In the case of positively charged atoms (for example, hydrogen atoms bound to atoms other than carbon), the directionality can be computed by calculating the dot product of the vector to the atom, and the vector to the centroid atoms to which the positively-charged atom is attached. The distances and directionalities provide a mathematical description of the surface of the compound that is purely local. The similarity of one molecule to another can then be computed by comparing the reference point weights and distances.

The similarity of one molecule to another, each in a particular conformation and alignment in a single coordinate frame, is defined in terms of the differences in observations made at a set of observation points on a uniform three-dimensional grid with a spacing $\Xi_0$. The positions of the points are denoted $o_i$. At each point, a weight is defined to limit the points that contribute to the subsequent similarity computation to those that are on the outside of one or another of the two molecules.

At each point, for each molecule, three distances are computed: the minimum distance to the VdW surface, the minimum distance to a hydrogen-bond acceptor or negatively charged atom, and the minimum distance to a hydrogen-bond donor or positively charged atom. In addition, a directionality term is computed for the observations of polar moieties. This corresponds to the directional concordance of the vector from the point to the polar atom and the atom's favored interaction vector.

The similarity between two molecules is simply a normalized sum of weighted Gaussian-like functions of differences in distances from observation points to the molecules. The equations are presented top-down:

$$f(a, b) = \frac{\sum_i (w_i^a + w_i^b) \begin{bmatrix} \sigma(s_i^a - s_i^b, \lambda_1) + \\ \max(S_i^{a+}, S_i^{b+})\sigma(s_i^{a+} - s_i^{b+}, \lambda_1)\sigma(S_i^{a+} - S_i^{b+}, \lambda_2) + \\ \max(S_i^{a-}, S_i^{b-})\sigma(s_i^{a-} - s_i^{b-}, \lambda_1)\sigma(S_i^{a-} - S_i^{b-}, \lambda_2) \end{bmatrix}}{\sum_i (w_i^a + w_i^b)[1 + \max(S_i^{a+}, S_i^{b+}) + \max(S_i^{a-}, S_i^{b-})]}$$

$s_i^a = \min(d(o_i, a_j) - r_j)$ $w_i^a = \sigma(s_i^a - \lambda_3, \lambda_4)$ $S_i^a = (1 + c_j)\omega((u_{ij} \cdot v_j) - \lambda_5, \lambda_6)$ $\sigma(x, \lambda) = e^{(-x^2/\lambda)}$ $\omega(x, \lambda) = \dfrac{1}{1 + e^{-x/\lambda}}$ Equation 1 defines the similarity f of molecules a and b. It is the sum over all observation points i of the weighted difference in observations (s and S) of the two molecules. Equation 2 defines the direct observations of molecular surface distances, where d is Euclidean distance, $o_i$ denotes position of observer i, $a_j$ denotes position of atom j, and $r_j$ denotes the Van der Waals ("VdW") radius of atom j. The atom set a can be either the full atom set a, the positive atom set $a^+$, or the negative atom set $a^-$. Equation 3 defines the observation point weighting based on a Gaussian-like function v of the nearest distance to the molecular surface. Equation 4 defines the polar strength component, dependent on a sigmoidal function ω of directionality weighted by a formal charge term (for the atoms sets $a^+$ and $a^-$). In that equation, j denotes the atom of a with the surface nearest to $o_i$, and $c_j$ denotes its charge. The vectors $u_{ij}$ and $v_j$ denote the direction from $o_i$ to $a_j$ and from $a_j$ to the centroid of its substituents, respectively.

Assignment to the sets a, $a^+$, and $a^-$ is done heuristically and is designed to account for the common cases well. The scheme is similar to that used by Hammerhead and Compass. See A. N. Jain, *J Comp-Aided Mol Des* (1996) 10:427–40; A. N. Jain et al., *J Med Chem* (1995) 38:1295–307. All atoms belong to the set a. All hydrogen atoms connected to non-carbon atoms are identified as positive atoms (in the set $a^+$) as are formally positively charged atoms. All oxygen atoms are identified as negative atoms (in the set $a^-$). Sulfur atoms not involved in disulfides or bonded to oxygen atoms are in $a^-$. Nitrogen atoms with three substituents not bonded to hydrogen that are non-planar with respect to their substituents are in $a^-$. All atoms with no formal charge are assigned a charge of 0. Atoms with positive formal charge distribute the total charge over any attached hydrogen atoms. Atoms with negative formal charge distribute the total charge across any resonant atoms (for example, the negative charge of a carboxylate is distributed between the two oxygen atoms).

For the examples reported below, $\lambda_0$ was 2.0 Å, $\lambda_1$ was 2.0, $\lambda_2$ was 0.5, $\lambda_3$ was 4.0, $\lambda_4$ was 0.2, $\lambda_5$ was 0.5, and $\lambda_6$ was 0.3. The parameters were not varied to optimize the performance of the technique on the separability problem or geometric prediction task. They were chosen primarily for computational speed. Other parameter sets were not systematically explored. For the similarity computation, only those observation points whose weight exceeded 0.1 were considered.

There are two problems in similarity optimization of one molecule to another. The first is rigid alignment of one molecule, or fragment, to another. The second is conformational optimization superimposed onto the alignment problem. The conformational optimization problem is solved as in Hammerhead (W. Welch et al., *Chem and Biol* (1996) 3:449–62), with a process of fragmentation, conformational search, alignment and scoring, and reconstruction from high-scoring aligned fragments. The alignment optimization method differs substantially from Hammerhead and is described here.

As mentioned above, all measurements made of the molecules in the similarity definition are local. So, a molecule that is arbitrarily translated and rotated from an initial position will still have a set of observation points that are measuring roughly the same values. Certainly this is true if the observation grid is arbitrarily dense. The problem of optimizing the alignment of one molecule to another is reduced to finding corresponding sets of observers, where each corresponding pair must yield a high local score according to the similarity function. Of course, the internal geometries of the corresponding point sets should also be consistent.

In the examples below, matching point-pairs from observations of different molecules were generated that had high local similarity (>0.7). From these, triples of point pairs were identified where each edge length difference was small (<1.5 Å) and each edge was greater than 4.5 Å in length. For each matched triangle pair, an alignment was computed to superimpose one to the other. Similar transforms were grouped and incremented in score, with the resulting high-scoring transforms being applied to the molecule to be aligned. Each resulting alignment was then evaluated according to the similarity function.

Since the similarity function is continuous and piecewise differentiable, gradient-based optimization was utilized on partially matched molecules as well as the final alignments. A restraining term preventing excessive steric clashes was employed in the conformational sampling process as well as the conformational optimization process as in Hammerhead (A. N. Jain 1996, supra; J. Ruppert et al., *Protein Science* (1996) 6:524–33).

Similarity Estimation

For the experiments on separability, similarity optimizations were carried out on each of the related molecules to each other (not including the identity mapping) as well as on comparisons of randomly chosen unrelated pairs. For each comparison (molecule A to molecule B), the target molecule B was conformationally sampled, and the similarity reported was the average of the optimized match of A to each of the conformations of B. In this manner, the ability of A to mimic B was measured. Note that A to B is different than B to A, so both measurements are included in the resulting distribution.

A maximum of ten conformations was used for sampling the target molecules for matching. The conformations were selected to be maximally different by rms deviation. Also, in the interests of computational speed, a maximum of ten conformations were used in sampling the fragments of the molecules to be aligned. Control experiments to determine the impact of the conformational subsampling showed that there was not a significant impact on the estimated similarity scores. Note that for ligands that were identical (a very small fraction of the related pairs used), the morphological method still was required to match a molecule to sampled conformations of itself beginning from unrelated conformations. For the topological method, these pairs automatically yielded similarities of 1.

The topological similarity technique was applied to the same set of related and unrelated pairs using the Daylight Toolkit and the supplied contributed code for SMILES format generation (syb2smi) as well as for the Tanimoto similarity computation (simatrix). The default parameters were employed.

Implementation and Speed

The program is implemented in C and runs on Macintosh, SGI, and PC platforms. A typical full alignment optimization (no conformational component) takes less than 2 seconds on an SGI R10000. Using the conformation subsampling alluded to above, alignment of flexible molecules scales roughly linearly, with molecules having 1 rotatable bond being optimized in approximately 5 seconds, 3 rotatable bonds in 10 seconds, 5 in 15 seconds, and so on. The same algorithms can be implemented in other languages, and on other platforms and operating systems. The following code is presented as an illustration.

The code functionality is described here top-down, beginning with the top-level function flex_align:
void flex_align(Conformer *in_conf1, Conformer *in_conf2, Conformer **final_conf, int nfinal)
The function seeks to flexibly align in_conf1 to in_conf2 through manipulation of the six alignment parameters of in_conf1 and the dihedral angles of the rotatable bonds of in_conf1 so as to maximize the computed similarity of the two.

The following contains code fragments in order, with explanations in text of the process.
if (mol1->nfrags==0) fragment_molecule(mol1);
(If the molecule has not been fragmented already, it is fragmented into roughly equally-sized fragments by breaking it at rotatable bonds.)
conf2=in conf2;
compute_features(conf2,NULL,0);

The features computed for conf2 are the target for conf1 to match. For each fragment of conf1, a sampled set of conformations of the fragment is aligned to conf2. By convention, fragment 0 consists of the entire molecule. The following sets up the housekeeping associated with searching each of the fragments (assuming they have not been previously searched).
for (fragnum=0; fragnum<=mol1->nfrags; ++fragnum) {
  for (i=0; i<=mol1->nfrags; ++i) {
    in_conf1->actfrag[i]=0;
  }
  in_conf1->actfrag[0]=0;
  in_conf1->actfrag[fragnum]=1;
  if (mol1->frag_confs[fragnum]==NULL) {
    fprintf(stderr,"Searching frag % d: ",fragnum);
    frag_confs[fragnum]=search_conf(in_conf1);
    mol1->frag_confs[fragnum]=frag_confs[fragnum];
  }
  else {
    frag_confs[fragnum]=mol1->frag_confs[fragnum];
  }
}
Once the fragments are set, they are aligned one at a time to the target conformer.
for (fragnum=0; fragnum<=mol1->nfrags; ++fragnum) {
  fprintf(stderr,"Frag % d: ",fragnum);
  nc1=0;
  for (conf1=frag_confs[fragnum]; conf1!=NULL; conf1=conf1->next) {
    ++nc1;
    fprintf (stderr,".");
    clear_features(conf1);
    add_stub(conf1);
    opt_conf1=
optimize_similarity(conf1,conf2,0,NULL,NULL);

The function add_stub takes the broken bonds emanating from the fragment (if any) and adds some bulk to the molecule at that point to prevent alignment of the severed part of the molecule with the target on a critical surface. The optimize_similarity function rapidly computes a set of high-scoring alignments of the fragment (discussed below). For fragment 0, the sampled whole molecule, the final scores are computed and added to the results to the nbest list of final conformations.
if (fragnum==0) {for (c1=opt_frag_confs[fragnum]; c1!=NULL; c1=c1->next) {
  tail_conf=copy_conformer(c1);
  compute_features(tail_conf,conf2->fs,0);
  score=compute_similarity(tail_conf,conf2);
  tail_conf->score=score;
  add_conf_nbest(tail_conf,best_conf,NBEST_CONFS);
  free_conformer(tail_conf);
  }
  free_conformers(opt_frag_confs[fragnum]);
  opt_frag confs[fragnum]=NULL;
  }
}

For the remaining aligned fragments, complete molecules are built by chaining from them the starting points and adding them to the nbest list of final conformations.
for (fragnum=1; fragnum<=mol1->nfrags; ++fragnum)
  fprintf(stderr, "Chaining frag % d: "fragnum);
  for (i=0; i<NBEST_FRAGS; ++i) {
    if (best_frag[fragnum][i]==NULL) continue;

conf=best_frag[fragnum][i];
    fprintf (stderr, ".") ;
    conf=chain_conf(conf,frag_confs,conf2);
    if (conf==NULL) continue;

add_conf_nbest(conf,best_conf,NBEST_CONFS);
    free_conformer(conf);
  {
}

If possible, any pairs of fragments that can be merged together from their resulting aligned positions are merged. This is done by checking the positions of the "stubs" to see if they are close enough.
if (mol1->nfrags>1) {
  merge_list=NULL;
  for (bnum=0; bnum<NMolBonds(mol1); ++bnum) {
    if (mol1->connections[bnum].frag==0) continue;

```
fragnum=Frag(mol1,BondStart(mol1,bnum));
fnum=Frag(mol1,BondEnd(mol1,bnum));
at1=BondStart(mol1,bnum);
at2=BondEnd(mol1,bnum);

fprintf(stderr,"Doing merges on bond % d: frag % d to
    frag % d: ",bnum,fragnum,fnum);
nm=0;
for (c1=opt_frag confs[fragnum]; c1!=NULL; c1=c1-
>next) {
    /* Now try to match the remaining fragment of the
        conformer */
    for (c2=opt_frag_confs[fnum]; c2!=NULL; c2=c2-
        >next) {
        /* Check the "heads" for good tails that are geo-
            metrically close */
        /* Check distance of new frag's atoms to old frag's */
        d1=V3Dist(Atom(c1,at1),Atom(c2,at2));
        d2=V3Dist(Atom(c1,at1),Atom(c1,at2));

if (fabs(d1-d2)>0.3) continue;
        ++nm;
        if (nm % 1000==0) fprintf(stderr,".");

merge=new_merge( );
        merge->confs[fragnum]=c1;
        merge->confs[fnum]=c2;
        merge->nfrags=2;

add_merge(c1,merge);
        add_merge(c2,merge);

free_merge(merge);
    }
  }
}
```

Since merging is an expensive process itself, it is preferred to first perform a pseudo similarity computation to see which of the potential merges are the best. The already computed features from the aligned fragments are used in order to compute an estimate of what the features of the merged fragments will look like.

```
fprintf(stderr,"\nMergesim:");
nm=0;
for (fragnum=1; fragnum<=mol1->nfrags; ++fragnum) {
    for (mconf=opt_frag_confs[fragnum]; mconf
        !=NULL;
mconf=mconf->next) {
    for (merge=mconf->merges; merge !=NULL; merge=
        merge->next) }
    if (nm % 1000==0) fprintf(stderr,".");
    nf=0;
    for (k=1; k<=mol1->nfrags; ++k) {
        if (merge->confs[k]!=NULL) {
            mconfs[nf]merge->confs[k];
            ++nf;
        }
    }
    if (nf !=2) {
        continue;
    }

++nm;
```

```
    score=compute_merged_similarity(mconfs,nf,conf2);
        }
    }
}
fprintf(stderr,"(% d pair merges) ",nm);
```

Following the identification of the best potential merges, the fragment pairs are merged, and if the molecule is not complete, the result is chained as above. The last stage of flex_align is incremental adjustment of alignment and conformation of the best conformers thus far and storage in the final conformation list.

```
fprintf(stderr,"Polishing:");
nt=0;
for (j=0; j<NBEST_CONFS; ++j) {
    tail_conf=best_conf[j];
    if (tail_conf==NULL) continue;
    fprintf (stderr, ".");
    tscore=
optimize_similarity_lsearch(tail_conf,conf2,1.0);
    add_conf_nbest(tail_conf,final_conf,nfinal);
    ++nt;
}
fprintf(stderr,"\");
```

The resulting list of conformations are stored in the input array final_conf. The only function with complex behavior in the foregoing is optimize similarity. This is where the speed lies:

Conformer *optimize_similarity(Conformer *orig_conf1,
    Conformer *conf2, int nhint_at, int *hint_at, Vector3
    *hint)

This function optimizes the similarity of conf1 to conf2 by modifying the conf1 alignment. This is accomplished by finding matching features of high weight between conf1 and conf2, then building a correspondence between pairs of good matches that have compatible internal distances to yield triplets of matched pairs. The transformations that align the triplets are applied to a standard triple of points, and the score of each match is accumulated in a list of matches that evolves over the course of all transformations. The highest-scoring transformations yield good places from which to postulate high scoring overall alignments, since they are the result of many high scoring feature matches that all yield the same transformation. Since the actual feature computation is driving the choice of alignments (as opposed to some surrogate) the procedure will yield transformations near the global optimimum very often.

First, a canonical set of points used to bin the transformations is defined, then the conformation to be aligned is copied (so as to avoid destructive side-effects on the passed in conformation). Features are computed for conf1, along with bounding boxes for conf1 and conf2 (used to ensure non-degenerate superpositions).

```
canon[0].x=canon[0].y=canon[0].z=0.0;
canon[1]=canon[0]; canon[1].y=10.0;
canon[2]=canon[0]; canon[2].z=10.0;
conf1=copy_conformer(orig_conf1);
compute_features(conf1,NULL,0);

bounding_box_points(conf1,corners1);
bounding_box_points(conf2,corners2);
```

Matching triples (more than ntriple_thresh) are located by examining highly weighted observation points (those that observe formally charged polar moieties are the most highly weighted). A high threshold for local similarity (sthresh) is set initially, but reduced if insufficient matching pairs of points are found. The initial process results in a set of matching point pairs.

```
    if (nhint_at<=0) ntriple_thresh=nt_thresh;
    else ntriple_thresh=5;
    sthresh=3.0;
    n_matched=0;
    ntriples=0;
    for (nmatch_thresh=200; nmatchthresh<500;
nmatch_thresh+=50) {
        head_match=NULL;
        if (sthresh<1.0) {
            wthresh=wthresh*0.8;
            fthresh=fthresh*0.8;
            sthresh=2.5;
        }
        for (sthresh=sthresh−0.5; sthresh>1.0; sthresh+=−
0.5) {
            nmatch=0;
            for (f1=0; f1<conf1->fs->n; ++f1) {
                if (conf1->fs->feature[f1].w<wthresh) continue;
            for (f2=0; f2<conf2->fs->n; ++f2) {
                if (conf2->fs->feature[f2].w<wthresh) continue;

if (fabs(conf1->fval[f1].stc-conf2->fval[f2].stc)
                    >0.5) continue;
                if (((conf1->fval[f1].acc_s>0.7) || (conf2->fval[f2]
                    .acc_s>0.7)) &&
                    (fabs(conf1->fval[f1].acc-conf2->fval[f2].acc)
                        >0.5)) {
                    continue;
                }
                if ((((conf1->fval[f1].don_s>0.7) (conf2->fval[f2]
                    .don_s>0.7)) &&
                    (fabs(conf1->fval[f1].don-conf2->fval[f2].don)
                        >0.5)) {
                    continue;
                } feature_sim(conf1,f1,conf2,f2,&sim,&str);
            score sim/str;
            if (score<fthresh) continue;
            if (sim<sthresh) continue;

new_match=(FMatch *) calloc(1,sizeof(FMatch));
            ++nmatch;
            new_match->f1=f1;
            new_match->f2=f2;
            new_match->f1pt=conf1->fs->feature[f1].pt;
            new_match->f2_pt=conf2->fs->feature[f2].pt;
            new_match->score=score;
            new_match->sim=sim;
            new_match->str=str;
```

Once a set of matching point pairs is obtained, the algorithm determines triples of point pairs, where the internal distances of observers of conf1 are similar to the internal distances of observers of conf2. This is done in a triply-nested loop through the pair matches. At each step, the distances are checked to make sure triangles of the same size are constructed.

```
    nmatchi=0;
    ngold=0;
    max_bbo=SMALL;
        for (matchi=head_match; matchi !=NULL; matchi=
            matchi->next) { ok_hint=0;
    for (i=0; i<nhint_at; ++i)
        dist1=V3Dist(&(matchi->f1_pt),&(hintpos[i]));
        dist2=V3Dist(&(matchi->f2_pt),&(hint[i]));
        if (fabs(dist1-dist2)<bfrag_thresh) ok_hint+=1;
    }
    if (ok_hint<nhint_at) continue;

++nmatchi;
    if (nmatchi>ni) break;
    if ((nmatchi>6) && (ntriples>ntriple_thresh)) break;
    if ((nhint_at>0) && (ntriples>ntriple_thresh)) break;

nmatchj=0;
    for (matchj=matchi->next; matchj !=NULL; matchj=
        matchj->next) { if (matchi->f1==matchj->f1) continue;
    if (matchi->f1==matchj->f2) continue;
    if (matchi->f2==matchj->f1) continue;
    if (matchi->f2==matchj->f2) continue;
    /* Make sure that the distance between the ith f1 and jth
        f1 is >threshold */
    pti1=&(matchi->f1_pt);
    ptj1=&(matchj->f1_pt);
    f1dist=V3DistSquared(pti1,ptj1);
    if (f1dist<dthresh) continue;

f1dist=sqrt(f1dist);
    ++ndist;

/* Make sure that the f1 feature distance is similar to the
        f2 feature distance */
    pti2=&(conf2->fs->feature[matchi->f2].pt);
    ptj2=&(conf2->fs->feature[matchj->f2].pt);
    f2dist=V3Dist(pti2,ptj2);
    ++ndist;
    if (fabs(f1dist-f2dist)>d2thresh) continue;

++nmatchj;
    if (nmatchj>nj) break;
    nmatchk=0;
    for (matchk=matchj->next; matchk !=NULL; matchk=
        matchk->next) {
        if (matchk->f1==matchj->f1) continue;
        if (matchk->f1==matchj->f2) continue;
        if (matchk->f2==matchj->f1) continue;
        if (matchk->f2==matchj->f2) continue;
        if (matchk->f1==matchi->f1) continue;
        if (matchk->f1==matchi->f2) continue;
        if (matchk->f2==matchi->f1) continue;
        if (matchk->f2==matchi->f2) continue;
        ok_hint=0;
        for (i=0; i <nhint_at; ++i) {/* Make sure that our feat
            match is consistent with this spatial match */
            dist1=V3Dist(&(matchk->f1_pt),&(hintpos[i]));
            dist2=V3Dist(&(matchk->f2_pt),&(hint[i]));
            if (fabs(dist1-dist2)<bfrag_thresh) ok_hint+=

}
    if (ok_hint<nhint_at) continue;

ptk1=&(matchk->f1_pt);
    ptk2=&(matchk->f2_pt);

/* Make sure that the new f1 is appropriate distance-
        wise */
```

```
f1dist=V3DistSquared(ptk1,pti1);
if (f1dist<dthresh) continue;
f1dist=sqrt(f1dist);
++ndist;
f2dist=V3Dist(ptk2,pti2);
++ndist;
if (fabs(f1dist-f2dist)>d2thresh) continue;

f1dist=V3DistSquared(ptk1,ptj1);
if (f1dist<dthresh) continue;
f1dist=sqrt(f1dist);
++ndist;
f2dist=V3Dist(ptk2,ptj2);
++ndist;
if (fabs(f1dist-f2dist)>d2thresh) continue;
++nmatchk;
if (nmatchk>nk) break;
```
This provides i,j,k that define a good match between the features of conf1 and conf2 and match in terms of internal distances. From this, a transform that minimizes the rms deviation of the points is computed:
```
/* Compute the transform and apply it to conf1, check sim
*/
vec1[0]=*pti1;
vec1[1]=*ptj1;
vec1[2]=*ptk1;
vec2[0]=*pti2;
vec2[1]=*ptj2;
vec2[2]=*ptk2;
psim=(matchi->sim+matchj->sim+matchk->sim);
lsq_fit_alignment(vec1, vec2, NULL, 3, &align,
    NULL);
```
The transform is applied to the canonical set of points. The new set of points is merged into the list of accumulating point alignments according to a Gaussian function of the difference between the new set and each existing set. Bounding box overlap between the corners of conf1 and the corners of conf2 is used to eliminate many spurious alignments quickly.
```
xform_points_by_alignment(canon,new_canon,
    &align, 3);
xform_points_by_alignment(corners1,new corners1,
    &align, 7);
bbo=bounding_box_overlap(new_corners1,corners2, 7,
    7);
if (bbo<0.7)
    if (rms<2.0) fprintf(stderr,"@bbo");
    continue;
if (bbo>max_bbo) max_bbo=bbo;

total_weight=0.0;
for (c=0; c<n_matched; ++c) {
    dist=
V3DistSquared(&(new_canon[0]),&(matched[c].vec[0]))+
V3DistSquared(&(new_canon[1]),&(matched[c].vec[1]))+
V3DistSquared(&(new_canon[2]),&(matched[c].vec[2]));
    dist/=3.0;
    /* Add this point in using a gaussian weighting relative
        to distance */
    weight=gauss(dist,5.0);

if (weight>0.1) {
        matched[c].score+=(weight*psim);
        matched[c].total_sim+=(weight*score);
        for (m=0; m<3; ++m)

matched[c].vec[m].x=
((matched[c].vec[m].x*matched[c].n)+
(weight*new_canon[m].x))/(matched[c].n+weight);
            matched[c].vec[m].y=
((matched[c].vec[m].y*matched[c].n)+
(weight*new_canon[m].y))/(matched[c].n+weight);
            matched[c].vec[m].z=
((matched[c].vec[m].z*matched[c].n)+
(weight*new_canon(m).z))/(matched[c].n+weight);
        }
        matched[c].n+=weight;
        total_weight+=weight;
    }
}
if (total_weight<0.5) {/* No close enough guys
*/
    total_weight+=1.0;
    matched[n_matched].rms=rms;
    matched[n_matched].vec[0]=new_canon[0];
    matched[n_matched].vec[1]=new_canon[1];
    matched[n_matched].vec[2]=new_canon[2];
    matched[n_matched].score=psim*total_weight;
    matched[n_matched].total_sim=score*total_weight;
    matched[n_matched].n=total_weight;
    matched[n_matched].init_score=score;
    matched[n_matched].align=align;
    ++n_matched;
}
++ntriples;
}
}
}
if (ntriples>ntriple_thresh) break;
fprintf(stderr,"@");
    match=head_match;
    while (match !=NULL)
        tmp_match=match;
        match=match->next;
        free(tmp_match);
    }
    head_match=NULL;
}
```

At this point, the procedure has provided a list of matches, each of which has a score corresponding to the accumulated scores of the triangle matches that were accumulated into the match. The nbest different of these matches are then determined for further processing by using an estimate of the actual similarity that would result from applying the transforms represented by the matches to conf1. The estimate is obtained by transforming the observation points of conf1 and finding the nearest observation points of conf2 and using those pairs to compute the similarity. This is faster than recomputing the features of conf1 and then computing the similarity, and so it is used as a filter. The mechanics of the nbest reduction are not shown below.
```
max_score=SMALL;
for (c=0; c<n_matched; ++c)
    matched[c].total_sim=matched[c].total_sim/matched[c]
    .n;
```

```
    if (matched[c].score>max_score) max_score=matched
        [c].score;
}
ntriples=0;
for (c=0; c<n_matched; ++c) {
    if (matched[c].score<0.2*max_score) {
        if (matched[c].rms<2.0) {
            fprintf(stderr,"@low");
        }
        matched[c].score=0.0;
        continue;
    }
    if (matched[c].score>=0.2*max_score)
        lsq_fit_alignment(canon, &(matched[c].vec[0]),
            NULL, 3, &align, NULL); score=0.0;

xform_points_by_alignment(ofeature,nfeature,&align,
    conf1->fs->n);
psim=0.0;
pstr=0.0;
for (f2=0; f2<conf2->fs->n; ++f2) }
    if (conf2->fval[f2].w<0.1) continue;
    min_dist=BIG;
    for (f1=0; f1<conf1->fs->n; ++f1) {
        if (conf1->fval[f1].w<0.1) continue;
        dist=V3DistSquared(&(nfeature[f1]),&(conf2->fs-
            >feature[f2].pt));
        if (dist<min_dist) {
            min_dist=dist;
            min_id=f1;
        }
    }
    if (min_dist<LAMBDASQ) {
        feature_sim(conf1,min_id,conf2,f2,&sim,&str);
        psim+=sim;
        pstr+=str;
    }
    else {/* No match with this feature */
        pstr+=(conf2->fval[f2].w) *
            (1.0+/* Steric piece */
            (conf2->fval[f2].acc_s)+/* Acceptor piece */
            (conf2->fval[f2].don_s)); /* Donor piece */
    }
  }
    matched[c].score=psim/pstr;
  }
}
```

Next, the best transforms are applied to conf1, compute its new features, and the best of the final similarity matches are accumulated.
```
head conf=NULL;
max=SMALL;
for (c=0; c<nbest; ++c)
    if (bestm[c].score==0.0) continue;
    new conf=copy_conformer(orig_conf1);
    lsq_fit_alignment(canon, &(bestm[c].vec[0]), NULL, 3,
        &align, NULL);
    xform_points_by_alignment(oatom,new_conf->atom,
        &align, NAtoms(mol1));
    score=bestm[c].score;
    compute_features(new_conf,conf2->fs,0);
    score=compute_similarity(new_conf,conf2);
    new_conf->score=score;
    new_conf->next=head_conf;
    head_conf=new_conf;
    if (score>max)
        max=score;
        max_id=c;
    }
}
return (head_conf);
```

The resulting list of conformers is returned to the caller. Note that there has been no incremental optimization of alignment in this procedure. This procedure is designed to be as fast as possible in yielding a set of alignments of a conformer such that one of the alignments, when optimized incrementally, will yield the globally maximal conformation under the similarity function. It is the responsibility of the caller to perform whatever optimizations may be required.

Incremental alignment and conformational optimization is straightforward and makes use of a line-search (see optimize_similarity_lsearch). Many procedures for optimization of functions exist, and there are particularly fast ones for functions that have well-defined gradients as exist for the similarity function. However, the optimization cost is low compared to the matching process, and little time was spent implementing fancy optimization methods.

The actual computation of the similarity function is very straightforward, since the underlying computation is simply a comparison of the distances of points to spheres. The aforementioned manuscript provides the best roadmap available. The key functions are make_molecular_feature_set, which defines the set of significantly weighted observers of a molecule, compute_features, which computes the features of a molecule, and compute_similarity, which compares the features of two molecules that have had their features computes with respect to the same feature set.

The one complication has to do with feature sets. According to a strict reading of the similarity definition, one must compute the similarity of two aligned molecules on the basis of observations from any observation point that received significant weight from either molecule. Since molecules generally are unaligned, this would require recalculation of a joint observation set following each putative alignment of one molecule to another. In practice, a shortcut approximation is made where the active observation set is taken to be the set computed for the molecule that is the target of similarity optimization.

To make a final, complete, calculation of the similarity requires that one recompute the observation set for the aligned molecule (make_molecular_feature_set), merge the set with that of the target molecule (merge_molecular_feature_sets), recompute features for both molecules (compute_features), and compute the final similarity (compute_similarity). For molecules that have high similarity, this does not make much of a difference. For target molecules that are a fragment of the molecule to be aligned, it can make a significant difference. The feature set being used will ignore the excess pieces of the molecule being aligned and essentially only report the extent to which the target molecule is covered. This can be very useful behavior in assessing fragment similarity.

EXAMPLES

The following examples are provided as a guide for the practitioner of ordinary skill in the art. Nothing in the examples is intended to limit the claimed invention.

Example 1

Separability of Related from Unrelated Ligands

The work of Jones et al. on the GOLD docking technique provides a convenient dataset on which to test the ability of a similarity method to discriminate related molecules from unrelated ones (G. Jones et al., *J Mol Biol* (1997) 267: 727–48). The set includes 134 crystal structures of small molecules bound to proteins, where there are many cases of multiple different ligands bound to the same (or highly similar) proteins. In the case of pairs of molecules that bind the same site, one expects that an effective similarity technique will yield relatively high scores compared with randomly chosen pairs of molecules.

The following two lists reference the test case names in the GOLD dataset (G. Jones, supra). Ligands that formed covalent adducts with the protein were eliminated due to the difficulty in interpreting the atoms with partially filled valence. Enzymes with catalytically active $Zn^{++}$ ions were also eliminated from consideration due to the overriding influence of Zn-based interactions with specific small substructural components of the ligands.

All related pairs used: (1tng 1tni) (1tng 1tni) (1tng 3ptb) (1tni 1tng) (1tni 1tnl) (1tni 3ptb) (1tnl 1tng) (1tnl 1Tni) (1Tnl 3ptb) (3ptb 1Tng) (3ptb 1Tni) (3ptb 1Tnl) (1dwd 1etr) (1etr 1dwd) (1dri 4dfr) (4dfr 1drl) (1ghb 8gch) (8gch 1ghb) (1acj 1ack) (1ack 1acj) (1nis 1aco) (1aco 1nis) (6abp 1abe) (1abe 6abp) (1com 2cht) (2cht 1com) (1fki 1fkg) (1fkg 1fki) (1dbb 1dbj) (1dbb 2dbl) (1dbj 1dbb) (1dbj 2dbl) (2dbl 1dbb) (2dbl 1dbj) (1glp 1glq) (1glq 1glp) (1aaq 1hef) (1aaq 4phv) (1hef 1aaq) (1hef 4phv) (4phv 1aaq) (4phv 1hef) (1lah 1lst) (1lst 1lah) (1mrg 1aha) (1aha 1mrg) (1ive 2sim) (2sim 1ive) (2phh 1pbd) (1pbd 2phh) (1epb 1cbs) (1epb 1fen) (1cbs 1epb) (1fen 1epb) (6rsa 1rob) (1rob 6rsa) (1sr 1stp) (1stp 1srj) (1tka 1trk) (1trk 1tka) (1tph 7tim) (7tim 1tph) (1did 1die) (1did 1xid) (1did 1xie) (1die 1did) (1die 1xid) (1die 1xie) (1xid 1did) (1xid 1die) (1xid 1xie) (1xie 1did) (1xie 1die) (1xie 1xid)

All unrelated pairs used: (1aaq 1eed) (1aaq 1srj) (1aaq 1ive) (1abe 2lgs) (1abe 1drl) (1abe 1cdg) (1abe 1hdc) (1abe 1rds) (1acj 1srj) (1acj 1glp) (1acj 1hri) (1ack 3ptb) (1ack 2cgr) (1ack 1icn) (1ack 1icn) (1ack 5p2p) (1ack 1etr) (1ack 1byb) (1ack 1byb) (1ack 1hdc) (1acm 2cmd) (1acm 2lgs) (1acm 2phh) (1acm 1xie) (1acm 3cla) (1acm 3cla) (1acm 1did) (1acm 2gbp) (1aco 1com) (1aco 2gbp) (1aco 1tdb) (1aco 1ukz) (1aco 5p2p) (1aco 1poc) (1aco 1eed) (1aha 1ukz) (1aha 3hvt) (1aha 5p2p) (1aha 1glq) (1apt 1cbs) (1baf 1hsl) (1baf 1imb) (1baf 2dbl) (1baf 1com) (1bbp 6rsa) (1bma 1rds) (1bma 1hsl) (1bma 1com) (1byb 1slt) (1byb 1nco) (1byb 6rsa) (1byb 2r07) (1byb 1die) (1byb 1tka) (1byb 1wap) (1byb 1ack) (1byb 1ack) (1byb 1lst) (1byb 1mup) (1byb 3ptb) (1cbs 1icn) (1cbs 1eap) (1cbs 3tpi) (1cbs 1apt) (1cdg 1coy) (1cdg 1abe) (1cdg 1pbd) (1com 1aco) (1com 1ghb) (1com 2dbl) (1com 1baf) (1com 1fkg) (1com 1bma) (1coy 1mrk) (1coy 1cdg) (1coy 1xid) (1coy 1fkg) (1coy 4phv) (1coy 4cts) (1ctr 1icn) (1ctr 4fab) (1ctr 1dwd) (1ctr 2cgr) (1ctr 1did) (1ctr 2lgs) (1dbb 1mrk) (1dbb 8gch) (1dbb 4dfr) (1dbb 1mrg) (1dbb 1lst) (1dbj 1tka) (1dbj 2phh) (1dbj 2r07) (1dbj 1eed) (1did 2sim) (1did 1mrk) (1did 1acm) (1did 3tpi) (1did 1ldm) (1did 1ctr) (1die 5p2p) (1die 1byb) (1die 4phv) (1drl 1ulb) (1drl 1abe) (1drl 8gch) (1drl 1mrg) (1dr 1glq) (1drl 1wap) (1drl 1tka) (1drl 1lic) (1drl 2lgs) (1dwd 1hef) (1dwd 1ctr) (1dwd 1ukz) (1dwd 1wap) (1dwd 2lgs) (1eap1hdc) (1eap 1cbs) (1eap 8gch) (1eap 2sim) (1eap 1xie) (1eed 1aaq) (1eed 1tdb) (1eed 1dbj) (1eed 1rob) (1eed 3hvt) (1eed 2phh) (1eed 2cmd) (1eed 1aco) (1epb 7tim) (1epb 1lmo) (1epb 1poc) (1eta 1icn) (1eta 1ulb) (1eta 1fen) (1eta 1tph) (1etr 6rsa) (1etr 1tdb) (1etr 1ack) (1etr 1tph) (1fen 1eta) (1fkg 1coy) (1fkg 8gch) (1fkg 1com) (1fkg 1ulb) (1lkg 3ptb) (1fki 1tdb) (1fki 2mcp) (1fki 1hsl) (1ghb 1com) (1ghb 1mup) (1glp 1tdb) (1glp 2sim) (1glp 1hef) (1glp 1pbd) (1glp 1acj) (1glq 1lmo) (1glq 2cgr) (1glq 1slt) (1glq 1dri) (1glq 1srj) (1glq 1aha) (1hdc 1eap) (1hdc 1lmo) (1hdc 2cgr) (1hdc 1ack) (1hdc 1abe) (1hdc 1mrg) (1hef 1dwd) (1hef 2r07) (1hef 1glp) (1hef 1wap) (1hri 1icn) (1hri 8gch) (1hri 1nco) (1hri 4dfr) (1hri 1ida) (1hri 1acj) (1hsl 1iah) (1hsl 2lgs) (1hsl 1baf) (1hsl 2dbl) (1hsl 1bma) (1hsl 1snc) (1hsl 1fki) (1icn 1cbs) (1icn 1ctr) (1icn 1hri) (1icn 2r07) (1icn 1eta) (1icn 1mcr) (1icn 1lst) (1icn 6rsa) (1icn 1ack) (1icn 1ack) (1icn 1tph) (1icn 1xid) (1ida 1sit) (1ida 1mcr) (1ida 1hri) (1ida 2pk4) (1igj 1tdb) (1igj 6rsa) (1igj 1wap) (1igj 3tpi) (1imb 1tdb) (1imb 1slt) (1imb 1trk) (1imb 1baf) (1imb 1Tng) (1imb 1nco) (1imb 1rne) (1ive 7tim) (1ive 1mcr) (1ive 6rsa) (1ive 2ak3) (1ive 1Tni) (1ive 1aaq) (1iah 1hsl) (1lah 1tng) (1ldm 2cht) (1ldm 1did) (1ldm 1rob) (1ldm 1tdb) (1ldm 6rsa) (1lic 3tpi) (1lic 1drl) (1lmo 1glq) (1lmo 1hdc) (1lmo 1lst) (1lmo 1epb) (1lst 1icn) (1lst 1lmo) (1lst 1byb) (1lst 1tph) (1lst 1dbb) (1mcr 1ive) (1mcr 1ukz) (1mcr 1ukz) (1mcr 1ida) (1mcr 1icn) (1mcr 1tph) (1mdr 1pbd) (1mrg 6abp) (1mrg 1pbd) (1mrg 1drl) (1mrg 1mrk) (1mrg 3cla) (1mrg 1srj) (1mrg 1snc) (1mrg 1dbb) (1mrg 1poc) (1mrg 1hdc) (1mrk 1did) (1mrk 2gbp) (1mrk 3cla) (1mrk 1coy) (1mrk 1mrg) (1mrk 1dbb) (1mrk 2pk4) (1mup 2cht) (1mup 1ghb) (1mup 3cla) (1mup 1byb) (1nco 1byb) (1nco 3cla) (1nco 2cgr) (1nco 1hri) (1nco 1stp) (1nco 1imb) (1nis 3aah) (1nis 3ptb) (1nis 1rds) (1pbd 1mdr) (1pbd 1mrg) (1pbd 3aah) (1pbd 3aah) (1pbd 1cdg) (1pbd 1gip) (1pbd 2plv) (1poc 1epb) (1poc 1mrg) (1poc 2gbp) (1poc 1ulb) (1poc 1aco) (1rds 5p2p) (1rds 1bma) (1rds 2gbp) (1rds 1abe) (1rds 1nis) (1rne 2cgr) (1rne 1stp) (1rne 1imb) (1rob 3hvt) (1rob 2lgs) (1rob 1tph) (1rob 2cgr) (1rob 1eed) (1rob 1ldm) (1sit 1byb) (1sit 2ak3) (1sit 1glq) (1sit 1imb) (1sit 1ida) (1sit 1Tni) (1sit 1Tng) (1snc 2dbl) (1snc 1mrg) (1snc 6abp) (1snc 1xie) (1snc 1hsl) (1srj 1aaq) (1srj 1ulb) (1srj 1ulb) (1srj 4phv) (1srj 1glq) (1srj 1mrg) (1srj 1acj) (1stp 1tdb) (1stp 1nco) (1stp 1lme) (1tdb 1imb) (1tdb 1stp) (1tdb 1glp) (1tdb 1igj) (1tdb 3hvt) (1tdb 3hvt) (1tdb 5p2p) (1tdb 1fki) (1tdb 3tpi) (1tdb 1ldm) (1tdb 1etr) (1tdb 1eed) (1tdb 1aco) (1tka 6rsa) (1tka 1dbj) (1tka 3cla) (1tka 1drl) (1tka 1byb) (1tng 1lah) (1tng 3hvt) (1tng 1imb) (1tng 6rsa) (1tng 1slt) (1tni 1ive) (1tni 1ukz) (1Tni 6mt) (1Tni 1slt) (1Tnl 1wap) (1Tnl 8gch) (1tph 1xie) (1tph 2mcp) (1tph 1rob) (1tph 3aah) (1tph 1icn) (1tph 1ukz) (1tph 1lst) (1tph 1mcr) (1tph 1etr) (1tph 1eta) (1tph 3ptb) (1tph 3ptb) (1trk 2sim) (1trk 3aah) (1trk 1imb) (1ukz 1mcr) (1ukz 1mcr) (1ukz 1aha) (1ukz 1dwd) (1ukz 1aco) (1ukz 1tph) (1ukz 1Tni) (1ulb 1drl) (1ulb 1srj) (1ulb 1srj) (1ulb 3aah) (1ulb 5p2p) (1ulb 1eta) (1ulb 2r07) (1ulb 1fkg) (1ulb 1poc) (1wap 1dwd) (1wap 1drl) (1wap 2sim) (1wap 1hef) (1wap 1Tnl) (1wap 1igj) (1wap 1byb) (1xid 4cts) (1xid 6rsa) (1xid 1coy) (1xid 1icn) (1xie 2cmd) (1xie 2cht) (1xie 2lgs) (1xie 1tph) (1xie 2pk4) (1xie 1acm) (1xie 2plv) (1xie 1eap) (1xie 1snc) (2ak3 1slt) (2ak3 1ive) (2cgr 1glq) (2cgr 2pk4) (2cgr 2yhx) (2cgr 3aah) (2cgr 1me) (2cgr 4phv) (2cgr 1rob) (2cgr 1ack) (2cgr 1nco) (2cgr 1hdc) (2cgr 1ctr) (2cht 6abp) (2cht 1xie) (2cht 1mup) (2cht 1ldm) (2cht 5p2p) (2cmd 1acm) (2cmd 1xie) (2cmd 2pk4) (2cmd 2plv) (2cmd 1eed) (2dbl 1snc) (2dbl 4dfr) (2dbl 1com) (2dbl 1hsl) (2dbl 1baf) (2gbp 1mrk) (2gbp 1aco) (2gbp 1acm) (2gbp 1rds) (2gbp 1poc) (2lgs 1 hsl) (2lgs 1abe) (2lgs 4cts) (2lgs 1acm) (2lgs 1xie) (2lgs 1rob) (2lgs 1drl) (2lgs 1dwd) (2lgs 1ctr) (2mcp 1tph) (2mcp 1fki) (2mcp 2r07) (2phh 1acm) (2phh 1dbj) (2phh 2plv) (2phh 2plv) (2phh 1eed) (2pk4 2cgr) (2pk4 1xie) (2pk4 2cmd) (2pk4 1mrk) (2pk4 1ida) (2plv 6abp) (2plv 2r07) (2plv 1xie) (2plv 1pbd) (2plv 3aah) (2plv 2phh) (2plv 2phh) (2plv 2cmd) (2r07 1dbj) (2r07 1icn) (2r07 1byb) (2r07 1hef) (2r07 2plv) (2r07 2mcp) (2r07 1ulb) (2sim 1did) (2sim 1glp) (2sim 6abp) (2sim 1rap) (2sim 1trk) (2sim 1wap) (2yhx 2cgr) (3aah 1pbd) (3aah 1pbd) (3aah 1nis) (3aah 1trk) (3aah 2cgr) (3aah 1tph) (3aah 1ulb) (3aah 4dfr) (3aah 2plv) (3aah 3ptb) (3cla 1acm) (3cla 1acm) (3cla 1tka) (3cla 1mrg) (3cla 1nco) (3cla 1mup) (3hvt 1aha) (3hvt 1tdb) (3hvt 1tdb) (3hvt 1rob) (3hvt 1tng) (3hvt 1eed) (3ptb 1ack) (3ptb 1nis) (3ptb 3aah) (3ptb 1tph) (3ptb 1tph) (3ptb 1byb) (3ptb 1fkg) (3tpi 1did) (3tpi 1tdb) (3tpi 1cbs) (3tpi 1igj) (3tpi 1lic) (4cts 2lgs) (4cts 1xid) (4cts 4fab) (4cts 5p2p) (4cts 1coy) (4dfr 2dbl) (4dfr 5p2p) (4dfr 3aah) (4dfr 1hri) (4dfr 1dbb) (4fab 1ctr) (4fab 4cts) (4phv 2cgr) (4phv 1srj) (4phv 1die) (5p2p 1tdb) (5p2p 1aha) (5p2p 2cht) (5p2p 4dfr) (5p2p 1die) (5p2p 1ulb) (5p2p 1ack) (5p2p 4cts) (5p2p 1aco) (6abp 1mrg) (6abp 2cht) (6abp 2sim) (6abp 2plv) (6abp 1snc) (6rnt 1tni) (6rsa 1ive) (6rsa 1xid) (6rsa 1igj) (6rsa 1tka) (6rsa 1byb) (6rsa 1bbp) (6rsa 1etr) (6rsa 1icn) (6rsa 1ldm) (6rsa 1tng) (7tim 1ive) (7tim 1epb) (8gch 1drl) (8gch 1eap) (8gch 1fkg) (8gch 1hri) (8gch 1dbb) (8gch 1tnl)

Figure 4:
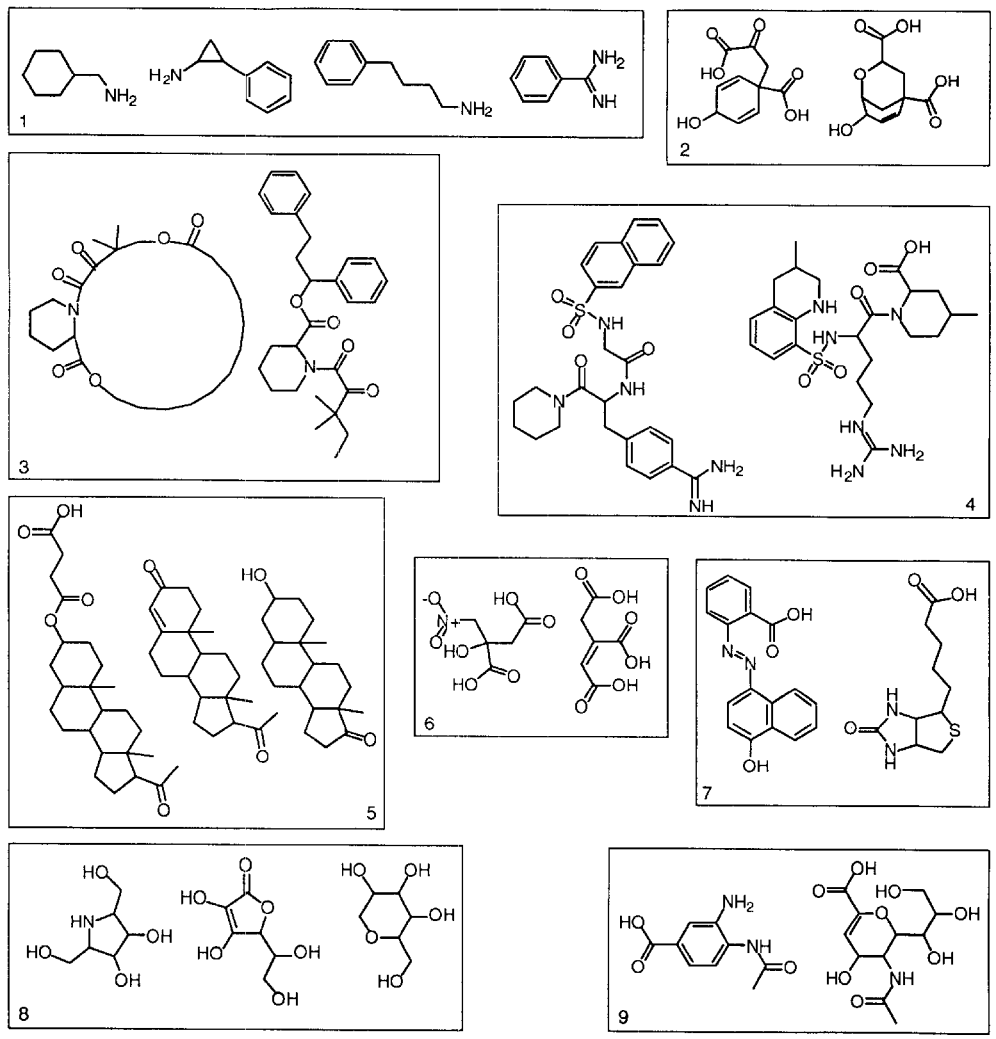
FIG. 4 shows a representative grouping of ligands.

FIG. 4 shows representative examples of grouped sets of ligands that were used to generate a population of pairwise molecular comparisons. The ligands in each group all bind competitively at the same or highly similar sites and were used to generate a list of positive example pairs. Beginning from random initial starting conformations, each ligand was matched to sampled conformations of each of the other related ligands by maximizing morphological similarity according to the protocol defined herein. The same procedure was followed for a large number of randomly selected pairs of ligands, each of which did not belong to the related pairs list.

Figure 5:
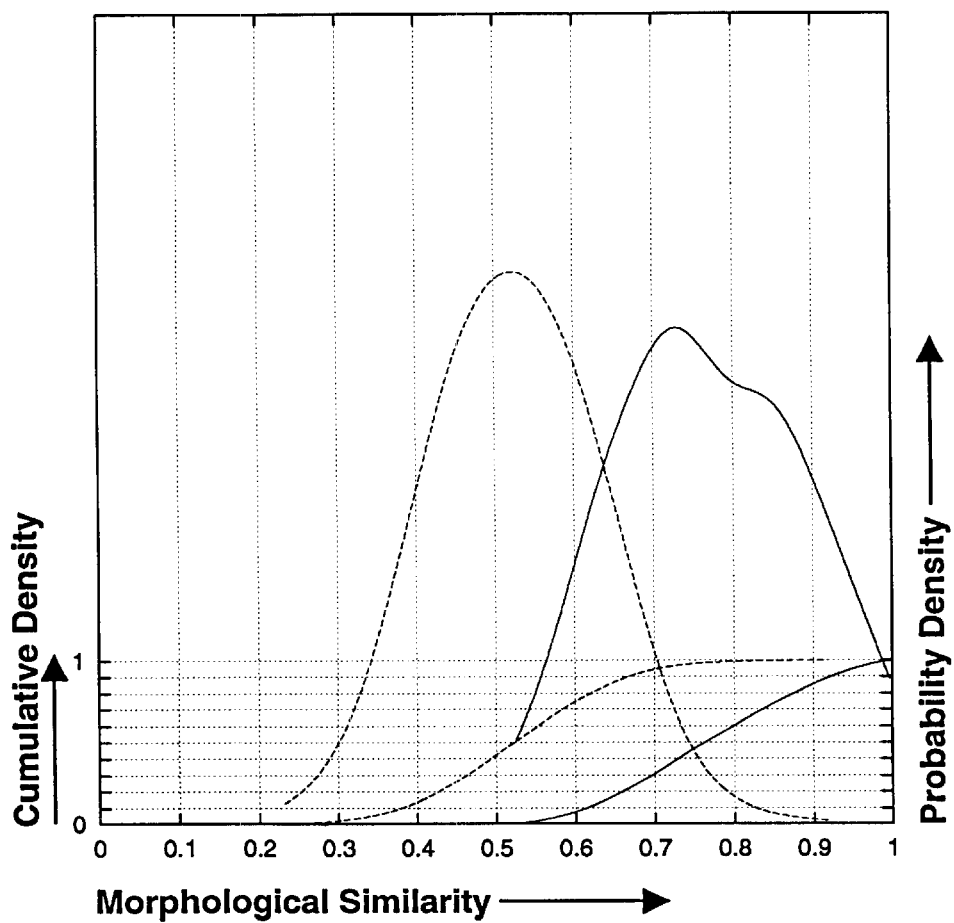
FIG. 5 shows the smoothed probability density functions and corresponding cumulative distribution functions for the two sets of data for the morphological similarity method.
Figure 6:
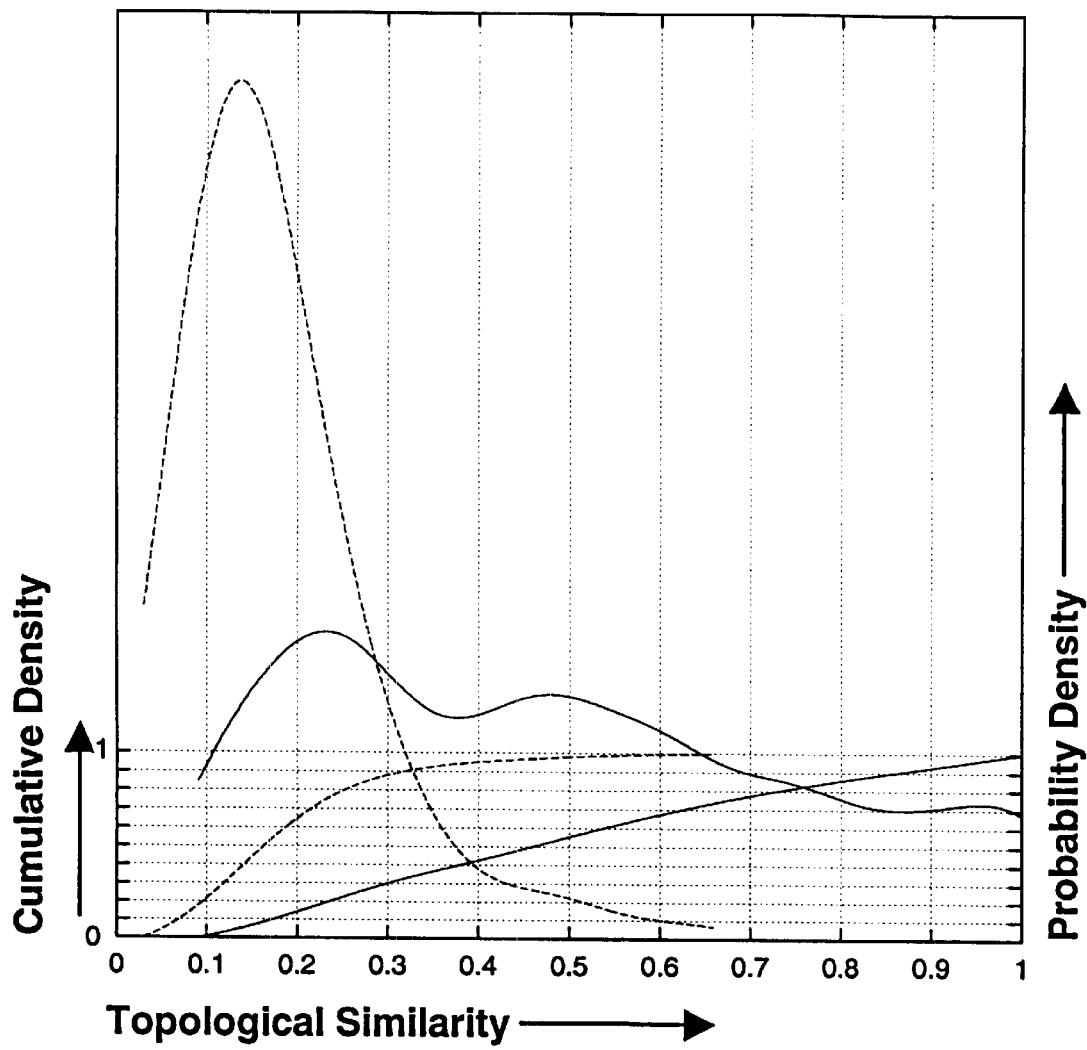
FIG. 6 shows the smoothed probability density functions and corresponding cumulative distribution functions for the two sets of data using the topological method.

FIG. 5 shows the smoothed probability density functions and corresponding cumulative distribution functions for the two sets of data for the morphological similarity method. The distributions are partially overlapping, but are separable to a large degree. FIG. 6 shows the same experiment using the topological method. Note that the distribution of related pairwise similarities is quite diffuse. However, the distribution of unrelated pairwise similarities remains partially separable from the broad distribution of the positives.

Figure 7:
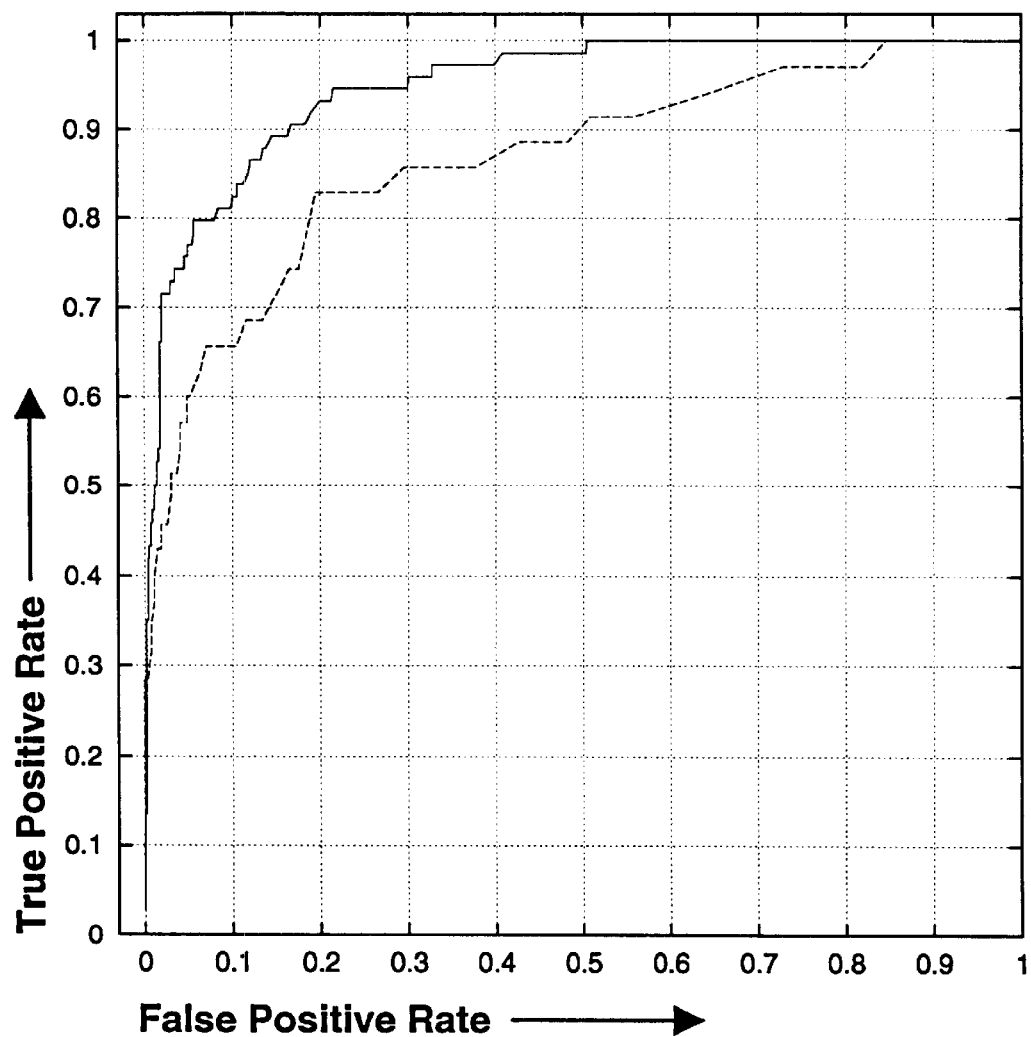
FIG. 7 shows the receiver operator characteristic curves obtained using morphological similarity (upper curve) and the topological method (lower curve).

Given that the two methods have different distributional characteristics, direct comparison of performance can be made using receiver operator characteristic curves. ROC curves for the two methods are plotted in FIG. 7. The abscissa corresponds to the false positive rate, and the ordinate corresponds to the true positive rate. For the morphological technique, it is possible to reject 95% of the unrelated pairs while rejecting only 23% of the related pairs. For the topological technique, to achieve 95% rejection of unrelated pairs, one must also reject 42% of the related pairs. This corresponds to an 87% increase in false negative rate to achieve statistical significance in a single pairwise comparison. Conversely, if one is willing to tolerate a particular false negative rate, say 30%, there is a 7-fold increase in the false positive rate (2% versus 14%). The morphological technique performs uniformly better than the topological technique at separating related from unrelated-molecules.

Figure 8:
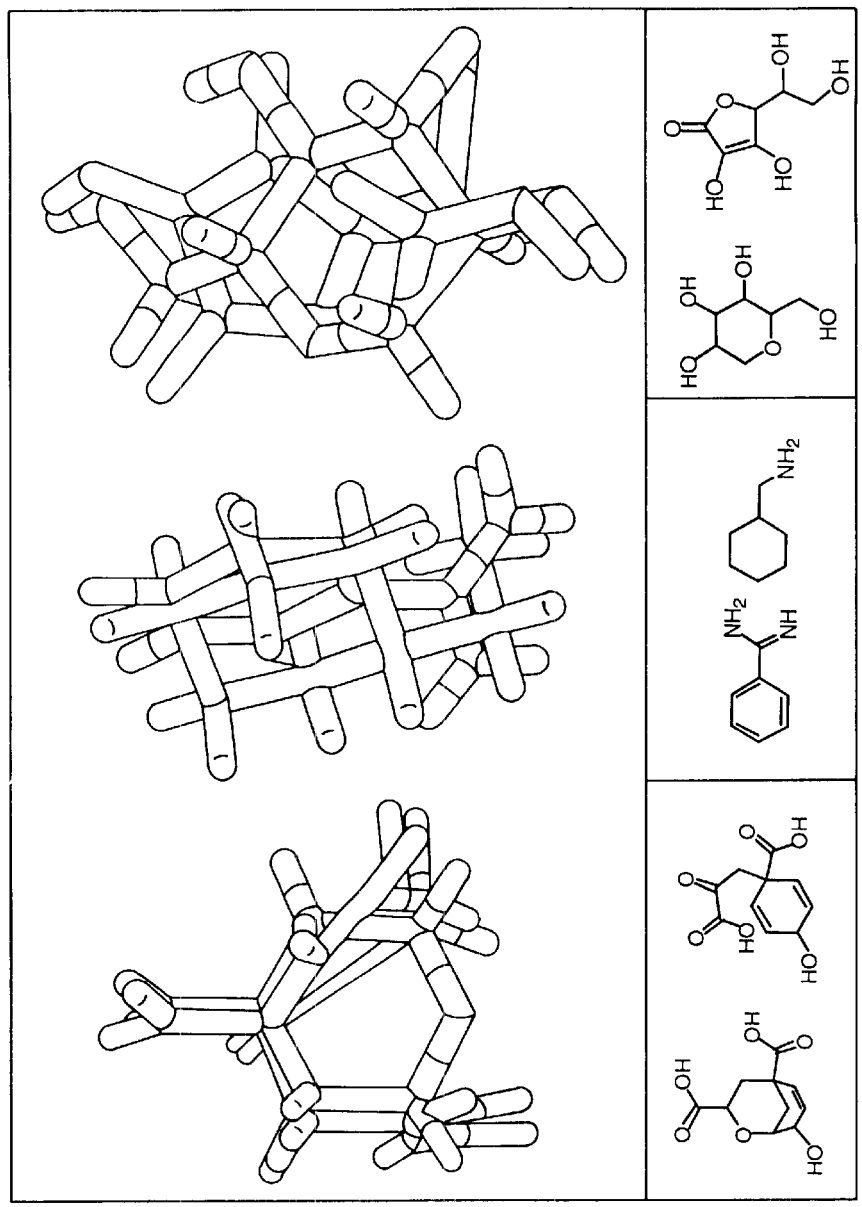
FIG. 8 shows three examples of typical pairs missed by topological similarity that are retained by morphological similarity at the p=0.05 cutoff of similarity in their maximally similar conformations and alignments.

FIG. 8 shows three examples of typical pairs missed by topological similarity that are retained by morphological similarity at the p=0.05 cutoff of similarity in their maximally similar conformations and alignments. It is easy to see why the morphological similarity technique works better than topological similarity. The molecules are able to adopt conformations that functionally display extremely similar surfaces to their cognate proteins.

Example 2

Predicted versus Observed Geometric Relationships of Ligands

The examples shown in FIG. 8 were compared with the experimentally determined geometric relationships within the active sites of the proteins. Where the mapping from 2D to 3D is non-obvious, arrows are used to indicate the corresponding parts. The proteins were aligned by minimizing the alpha carbon rms deviations.

For the ligands of chorismate mutase, there is almost no variation in the predicted versus observed conformations. In the trypsin case, the amine of the two aminomethylcyclohexane conformations and the C4 carbons are well matched, but the cyclohexane itself is flipped. Since benzamidine is symmetric, there is no way for the method to prefer one superposition versus the other of the two ligands. In the xylose isomerase case, the best-matching similarity induced model generates an incorrect mapping of functional elements of the two molecules. Ascorbic acid is rotated and shifted relative to the correct orientation. However, the gross relationship of the two molecules is maintained.

For competitive ligands numbering more than two, it is still possible to generate hypotheses of how such ligands are related, but it is slightly complicated by the combinatorics. There are order $N^2$ pairwise similarities to consider in seeking a set of conformers in a particular alignment that maximizes the joint similarity of all ligand pairs to each other. Any population fitness optimization procedure may be used to do this, and an approach similar to a genetic algorithm (See e.g., J. R. Koza, "Genetic Programming: On the Programming of Computers by Means of Natural Selection", MIT Press, Cambridge, Mass. 1992) was used in the following example where four diverse ligands were under simultaneous consideration.

Figure 9:
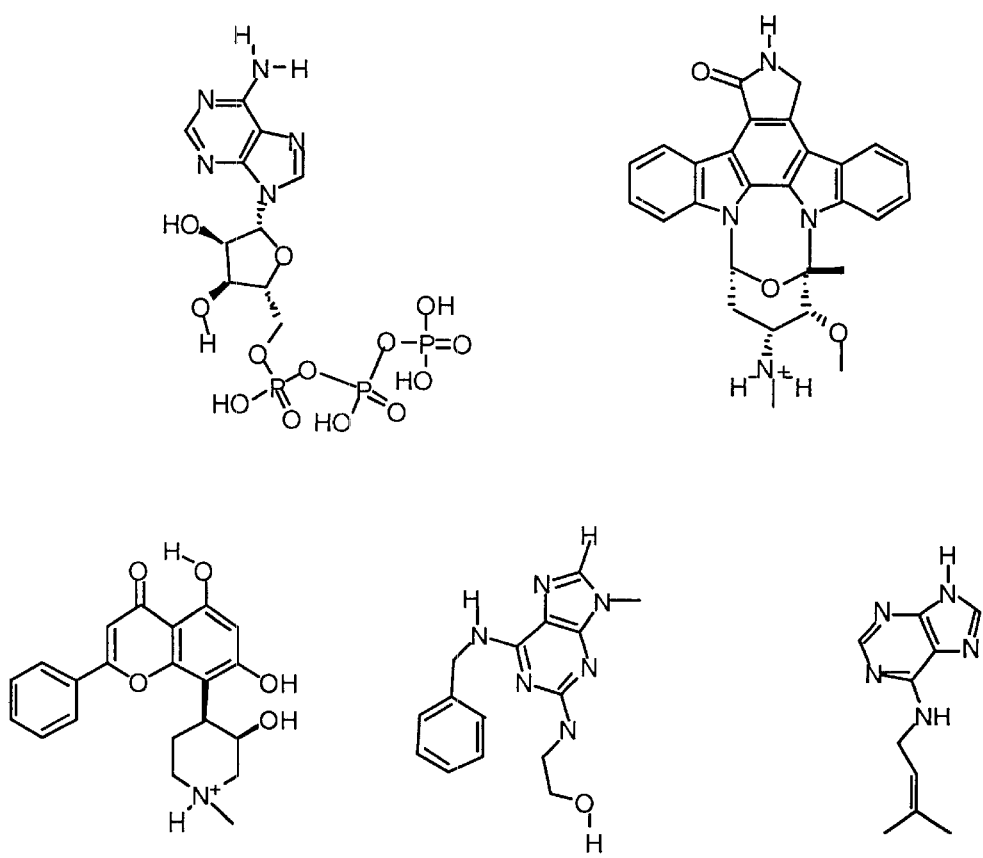
FIG. 9 shows five ligands of the CDK2 ATP-binding site: ATP, staurosporine, olomoucine, des-chloro-flavopiridol (DCF), and isopentenyl adenine (IPA).

FIG. 9 shows five ligands of the CDK2 ATP-binding site: ATP, staurosporine, olomoucine, des-chloro-flavopiridol (DCF), and isopentenyl adenine (IPA). The binding geometry of each ligand is known through crystallographic observation (S.-H. Kim et al., *Prog Cell Cycle Res* (1996) 2:137–45). The drawings in the figure depict the relative orientations in the binding site. Note that the three purine derivatives all have different orientations of the purine ring, and the other two molecules have very different underlying chemical structures.

Beginning from conformations unrelated to those observed crystallographically, the first four molecules were optimized for mutual similarity (ATP was truncated to adenosine for computational speed). ATP and staurosporine were aligned based on the alpha carbons of CDK2 (PDB references: 1HCK and 1AQ1, respectively). The calculated geometry shows that staurosporine extends its hydrophobic "arms" into areas not probed by ATP, and ATP extends into a phosphate binding domain that is organized around a magnesium ion.

Staurosporine was used as a convenient background on which to display the relative orientations of the other three ligands in the similarity-optimized model. IPA was optimized for summed similarity to the overlap of the first four, resulting in the last overlay. The structures of DCF and olomoucine bound to CDK2 are not yet available in the Protein Data Bank, but the optimized relationship shown corresponds well to those described in Kim et al., supra (this is cartooned with the 2D depictions). The minor exception has to do with the pendant phenyl of olomoucine, which is folded back in the similarity optimized model but is coincident with the phenyl of DCF in the experimentally observed conformation. Another overlay of olomoucine scores almost as well, with the molecule flipped left to right, superimposing its pendant phenyl onto the right-hand side of staurosporine and its NH onto the NH of staurosporine.

This predicted orientation of IPA corresponds quite closely to the experimentally observed relationship, despite the potentially complicating factor of a different purine orientation relative to adenosine and olomoucine. The mean similarity score of IPA against the other 4 was in the 81st percentile of all compounds from the separability experiment tested against the same model. Of the molecules that scored as well as IPA, nearly half were nucleoside analogs. IPA is a weak inhibitor, with an $IC_{50}$ of 50 $\mu$M versus CDK2 (Kim et al., supra). In a library of compounds, one could eliminate roughly 80% of the compounds and still detect IPA and other weak inhibitors using this crude unweighted similarity-based model.

To achieve better enrichment, more refined, possibly weighted, similarity models would need to be employed. In weighted models, lack of dependence of binding affinity to structural variation in ligands that are consistent with a single part of space could be represented explicitly with low weight. Similarly, tight dependence on specific molecular features would also be explicit (e.g. the common hydrogen-bonding interactions among the CDK2 ligands). Weighted models should yield more accurate geometric alignments, as well as offering the potential of quantitative predictions.

What is claimed:

1. A method for computing an alignment between a first molecule and a second molecule, the method comprising:

(a) providing a set of coordinate points;

(b) computing a molecular surface for said first molecule;

(c) selecting a first set of points that are approximately equidistant from the computed surface;

(d) computing a molecular surface for said second molecule;

(e) selecting a second set of points that are approximately equidistant from the computed surface of said second molecule;

(f) computing the distance from each selected point to the nearest hydrogen bond acceptor, and the distance from each selected point to the nearest hydrogen bond donor to provide a weighting for each point, said weighting further comprising the computed distance from the point to the computed molecular surface and direction of the hydrogen bond;

(g) identifying a first point in said first set having a weighting identical, within a predetermined tolerance, to the weighting of a first' point in said second set;

(h) identifying a second point in said first set having a weighting identical, within a predetermined tolerance, to the weighting of a second' point in said second set, wherein the distance between the first and second points in said first set is identical, within a predetermined tolerance, to the distance between the first' and second' points in said second set;

(i) identifying a third point in said first set having a weighting identical, within a predetermined tolerance, to the weighting of a third' point in said second set, wherein the distance between the first, second and third points in said first set is identical, within a predetermined tolerance, to the distance between the first', second' and third' points in said second set; and (j) transforming the coordinates of one set of coordinate point so that the first, second, and third identified points of the first set coincide with the first', second', and third' identified points of the second set within a predetermined tolerance to provide an alignment.

2. The method of claim 1, wherein said hydrogen bond direction is computed by computing the direction to the centroid of all atoms bound to the hydrogen bond donor or hydrogen bond acceptor.

3. The method of claim 1, further comprising optimizing the conformation of said first or second molecule after said alignment.

4. The method of claim 1, further comprising calculating the similarity of said first and second molecule, wherein said similarity comprises the normalized sum of weighted functions of differences in distances from the observation points to the molecular surfaces.

* * * * *